US008483828B2

(12) United States Patent
Libbus et al.

(10) Patent No.: US 8,483,828 B2
(45) Date of Patent: *Jul. 9, 2013

(54) COMBINED REMODELING CONTROL THERAPY AND ANTI-REMODELING THERAPY BY IMPLANTABLE CARDIAC DEVICE

(75) Inventors: Imad Libbus, St. Paul, MN (US); Bruce H. KenKnight, Maple Grove, MN (US); Julia Moffitt, Iowa City, IA (US); Yatheendhar D. Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 246 days.

This patent is subject to a terminal disclaimer.

(21) Appl. No.: 12/891,674

(22) Filed: Sep. 27, 2010

(65) Prior Publication Data
US 2011/0015692 A1    Jan. 20, 2011

Related U.S. Application Data

(63) Continuation of application No. 11/777,394, filed on Jul. 13, 2007, now Pat. No. 7,805,193, which is a continuation of application No. 10/850,341, filed on May 20, 2004, now Pat. No. 7,260,431.

(51) Int. Cl.
*A61N 1/365* (2006.01)
*A61N 1/05* (2006.01)

(52) U.S. Cl.
USPC ............ 607/23; 607/2; 607/6; 607/9; 607/17; 607/19

(58) Field of Classification Search
USPC .................... 607/2, 6, 9, 17, 19, 23
See application file for complete search history.

(56) References Cited

U.S. PATENT DOCUMENTS

| | | | |
|---|---|---|---|
| 4,777,960 A | 10/1988 | Berger et al. | |
| 4,791,931 A | 12/1988 | Slate | |
| 5,014,698 A | 5/1991 | Cohen | |
| 5,111,815 A | 5/1992 | Mower | |

(Continued)

FOREIGN PATENT DOCUMENTS

| EP | 0547734 A2 | 6/1993 |
|---|---|---|
| EP | 0555988 | 8/1993 |

(Continued)

OTHER PUBLICATIONS

"U.S. Appl. No. 10/850,341, Non-Final Office Action mailed May 31, 2006", 8 pgs.

(Continued)

*Primary Examiner* — Niketa Patel
*Assistant Examiner* — Christopher A Flory
(74) *Attorney, Agent, or Firm* — Schwegman Lundberg & Woessner, P.A.

(57) ABSTRACT

A method and device for delivering ventricular resynchronization pacing therapy in conjunction with electrical stimulation of nerves which alter the activity of the autonomic nervous system is disclosed. Such therapies may be delivered by an implantable device and are useful in preventing the deleterious ventricular remodeling which occurs as a result of a heart attack or heart failure. The device may perform an assessment of cardiac function in order to individually modulate the delivery of the two types of therapy.

20 Claims, 4 Drawing Sheets

U.S. PATENT DOCUMENTS

| | | | |
|---|---|---|---|
| 5,190,035 A | 3/1993 | Salo et al. | |
| 5,199,428 A | 4/1993 | Obel et al. | |
| 5,203,326 A | 4/1993 | Collins | |
| 5,269,301 A | 12/1993 | Cohen | |
| 5,291,400 A | 3/1994 | Gilham | |
| 5,318,592 A | 6/1994 | Schaldach | |
| 5,330,507 A | 7/1994 | Schwartz | |
| 5,391,190 A | 2/1995 | Pederson et al. | |
| 5,437,285 A | 8/1995 | Verrier et al. | |
| 5,522,854 A | 6/1996 | Ideker et al. | |
| 5,578,061 A | 11/1996 | Stroetmann et al. | |
| 5,626,624 A | 5/1997 | Schaldach et al. | |
| 5,645,570 A | 7/1997 | Corbucci | |
| 5,658,318 A | 8/1997 | Stroetmann et al. | |
| 5,682,901 A | 11/1997 | Kamen | |
| 5,690,681 A | 11/1997 | Geddes et al. | |
| 5,700,282 A | 12/1997 | Zabara | |
| 5,749,900 A | 5/1998 | Schroeppel et al. | |
| 5,755,671 A | 5/1998 | Albrecht et al. | |
| 5,891,044 A | 4/1999 | Golosarsky et al. | |
| 5,916,239 A | 6/1999 | Geddes et al. | |
| 5,935,081 A | 8/1999 | Kadhiresan | |
| 6,006,134 A | 12/1999 | Hill et al. | |
| 6,026,320 A | 2/2000 | Carlson et al. | |
| 6,035,233 A | 3/2000 | Schroeppel et al. | |
| 6,073,048 A | 6/2000 | Kieval et al. | |
| 6,134,470 A * | 10/2000 | Hartlaub | 607/14 |
| 6,144,878 A | 11/2000 | Schroeppel et al. | |
| 6,161,042 A | 12/2000 | Hartley et al. | |
| 6,178,349 B1 | 1/2001 | Kieval | |
| 6,246,909 B1 | 6/2001 | Ekwall | |
| 6,269,263 B1 | 7/2001 | Ohnishi et al. | |
| 6,272,377 B1 | 8/2001 | Sweeney et al. | |
| 6,285,907 B1 | 9/2001 | Kramer et al. | |
| 6,292,695 B1 | 9/2001 | Webster, Jr. et al. | |
| 6,358,201 B1 | 3/2002 | Childre et al. | |
| 6,370,424 B1 | 4/2002 | Prutchi | |
| 6,371,922 B1 | 4/2002 | Baumann et al. | |
| 6,390,986 B1 | 5/2002 | Curcie et al. | |
| 6,459,929 B1 | 10/2002 | Hopper et al. | |
| 6,480,733 B1 | 11/2002 | Turcott | |
| 6,511,500 B1 | 1/2003 | Rahme | |
| 6,522,926 B1 | 2/2003 | Kieval et al. | |
| 6,542,774 B2 | 4/2003 | Hill et al. | |
| 6,564,096 B2 | 5/2003 | Mest | |
| 6,571,121 B2 | 5/2003 | Schroeppel et al. | |
| 6,571,122 B2 | 5/2003 | Schroeppel et al. | |
| 6,611,713 B2 | 8/2003 | Schauerte | |
| 6,622,041 B2 | 9/2003 | Terry, Jr. et al. | |
| 6,628,987 B1 | 9/2003 | Hill et al. | |
| 6,690,971 B2 | 2/2004 | Schauerte et al. | |
| 6,824,538 B2 | 11/2004 | Chen | |
| 6,850,801 B2 | 2/2005 | Kieval et al. | |
| 7,069,070 B2 | 6/2006 | Carlson et al. | |
| 7,123,961 B1 | 10/2006 | Kroll et al. | |
| 7,245,967 B1 | 7/2007 | Shelchuk | |
| 7,260,431 B2 | 8/2007 | Libbus et al. | |
| 7,392,084 B2 | 6/2008 | KenKnight et al. | |
| 7,403,819 B1 | 7/2008 | Shelchuk et al. | |
| 7,499,744 B2 | 3/2009 | Carlson et al. | |
| 7,570,999 B2 | 8/2009 | Libbus et al. | |
| 7,572,226 B2 | 8/2009 | Scheiner et al. | |
| 7,587,238 B2 | 9/2009 | Moffitt et al. | |
| 7,657,312 B2 * | 2/2010 | Pastore et al. | 607/9 |
| 7,711,420 B2 * | 5/2010 | Baynham et al. | 607/9 |
| 7,805,193 B2 * | 9/2010 | Libbus et al. | 607/11 |
| 8,131,362 B2 * | 3/2012 | Moffitt et al. | 607/9 |
| 8,195,290 B2 * | 6/2012 | Brockway et al. | 607/3 |
| 2001/0020136 A1 | 9/2001 | Sweeney et al. | |
| 2002/0026222 A1 | 2/2002 | Schauerte et al. | |
| 2002/0058877 A1 | 5/2002 | Baumann et al. | |
| 2002/0072683 A1 | 6/2002 | Schroeppel et al. | |
| 2002/0107553 A1 | 8/2002 | Hill et al. | |
| 2002/0120304 A1 | 8/2002 | Mest | |
| 2002/0120306 A1 | 8/2002 | Zhu et al. | |
| 2002/0161410 A1 | 10/2002 | Kramer et al. | |
| 2002/0165586 A1 | 11/2002 | Hill et al. | |
| 2003/0004549 A1 | 1/2003 | Hill et al. | |
| 2003/0045909 A1 | 3/2003 | Gross et al. | |
| 2003/0060848 A1 | 3/2003 | Kieval et al. | |
| 2003/0060857 A1 | 3/2003 | Perrson et al. | |
| 2003/0060858 A1 | 3/2003 | Kieval et al. | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0105493 A1 | 6/2003 | Salo | |
| 2003/0114889 A1 | 6/2003 | Huvelle et al. | |
| 2003/0149450 A1 | 8/2003 | Mayberg | |
| 2003/0212440 A1 | 11/2003 | Boveja | |
| 2004/0049235 A1 | 3/2004 | Deno et al. | |
| 2004/0193231 A1 | 9/2004 | David et al. | |
| 2004/0230241 A1 | 11/2004 | Carlson et al. | |
| 2005/0065554 A1 | 3/2005 | KenKnight et al. | |
| 2005/0090719 A1 | 4/2005 | Scheiner et al. | |
| 2005/0096705 A1 | 5/2005 | Pastore et al. | |
| 2005/0149156 A1 | 7/2005 | Libbus et al. | |
| 2005/0261741 A1 * | 11/2005 | Libbus et al. | 607/3 |
| 2006/0195038 A1 | 8/2006 | Carlson et al. | |
| 2006/0206154 A1 | 9/2006 | Moffitt et al. | |
| 2006/0271115 A1 | 11/2006 | Ben-Ezra et al. | |
| 2007/0142871 A1 | 6/2007 | Libbus et al. | |
| 2008/0015648 A1 * | 1/2008 | Libbus et al. | 607/9 |
| 2008/0021507 A1 * | 1/2008 | Libbus et al. | 607/17 |
| 2008/0125843 A1 | 5/2008 | Ben-David et al. | |
| 2008/0234776 A1 | 9/2008 | KenKnight et al. | |
| 2010/0125307 A1 * | 5/2010 | Pastore et al. | 607/18 |

FOREIGN PATENT DOCUMENTS

| | | |
|---|---|---|
| WO | WO-9815319 A1 | 4/1998 |
| WO | WO-0044274 A2 | 8/2000 |
| WO | WO-0051680 A1 | 9/2000 |
| WO | WO-0176689 A2 | 10/2001 |
| WO | WO-02085448 A2 | 10/2002 |
| WO | WO-03020364 A2 | 3/2003 |
| WO | WO-03082080 A2 | 10/2003 |
| WO | WO-2004012814 A1 | 2/2004 |
| WO | WO-2004033036 A2 | 4/2004 |
| WO | WO-2005030325 A1 | 4/2005 |

OTHER PUBLICATIONS

"U.S. Appl. No. 10/850,341, Notice of Allowance mailed Apr. 5, 2007", 7 pgs.

"U.S. Appl. No. 10/850,341, Notice of Allowance mailed Nov. 30, 2006", 8 pgs.

"U.S. Appl. No. 10/850,341, Response filed Oct. 2, 2006 to Non Final Office Action mailed May 31, 2006", 10 pgs.

"U.S. Appl. No. 11/777,394, Final Office Action mailed Mar. 4, 2010", 9 pgs.

"U.S. Appl. No. 11/777,394, Non-Final Office Action mailed Jul. 24, 2009", 10 pgs.

"U.S. Appl. No. 11/777,394, Notice of Allowance mailed May 28, 2010", 4 pgs.

"U.S. Appl. No. 11/777,394, Response filed Nov. 24, 2009 to Non Final Office Action mailed Jul. 24, 2009", 9 pgs.

"U.S. Appl. No. 11/777,394, Response filed May 4, 2010 to Final Office Action mailed Mar. 4, 2010", 7 pgs.

"International U.S. Appl. No. PCT/US2005/017659, International Search Report and Written Opinion, mailed Aug. 26, 2005", 13 pgs.

* cited by examiner

COMBINED REMODELING CONTROL THERAPY AND ANTI-REMODELING THERAPY BY IMPLANTABLE CARDIAC DEVICE

CLAIM OF PRIORITY

This application is a continuation of and claims the benefit of priority under 35 U.S.C. §120 to U.S. patent application Ser. No. 11/777,394, filed on Jul. 13, 2007, now issued as U.S. Pat. No. 7,805,193, which is a continuation of and claims the benefit of priority under 35 U.S.C. §120 to U.S. patent application Ser. No. 10/850,341, filed on May 20, 2004, now issued as U.S. Pat. No. 7,260,431, which applications are hereby incorporated by reference herein in their entirety.

CROSS-REFERENCE TO RELATED APPLICATIONS

This patent application is related to and commonly assigned U.S. patent application Ser. No. 10/700,368 filed Nov. 3, 2003, now issued as U.S. Pat. No. 7,657,312, the disclosures of which are incorporated by reference.

FIELD OF THE INVENTION

This patent application pertains to methods and apparatus for the treatment of cardiac disease. In particular, it relates to methods and apparatus for improving cardiac function with electro-stimulatory therapy.

BACKGROUND

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction.

It has been shown that the extent of ventricular remodeling is positively correlated with increased mortality in post-MI and heart failure patients. It is with reversing and/or preventing such ventricular remodeling that the present invention is primarily concerned.

DETAILED DESCRIPTION

Figure 1:
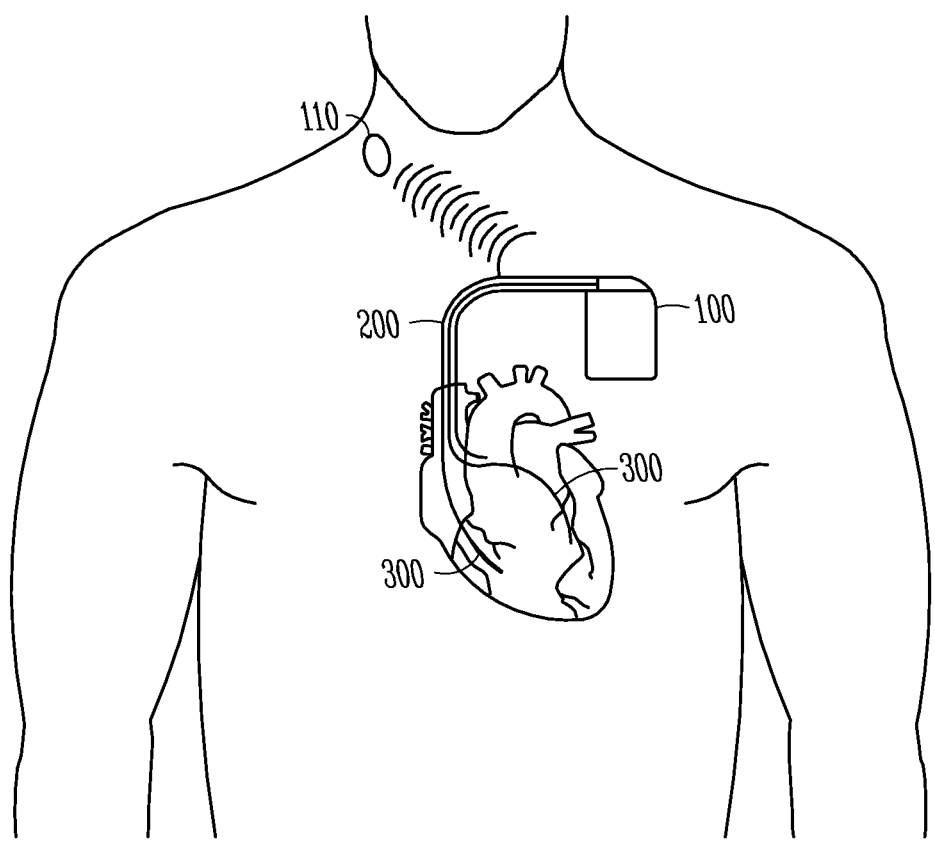
FIG. 1 illustrates the physical placement of an implantable cardiac device.

Clinical data has shown that cardiac resynchronization therapy (CRT), achieved through synchronized biventricular pacing, results in a significant improvement in cardiac function. It has also been reported CRT can be beneficial in preventing and/or reversing the ventricular remodeling that often occurs in post-MI and heart failure patients. As explained in detail below, the present invention relates to an implantable cardiac device capable of providing remodeling control therapy (RCT) by controlling ventricular activation with cardiac resynchronization pacing and providing anti-remodeling therapy (ART) by stimulating the baroreflex in order to inhibit sympathetic activity. The combined application of these two therapies provides a greater therapeutic benefit than either of them individually. The device controls ventricular activation through synchronized pacing of the right and left ventricles. In addition, the device may provide a combination of parasympathetic stimulation and sympathetic inhibition. Parasympathetic stimulation can be achieved through a nerve cuff electrode placed around the cervical vagus nerve bundle, while sympathetic inhibition can be achieved through baroreflex stimulation, either through a nerve cuff electrode placed around the aortic or carotid sinus nerve, or though a stimulation lead designed to stimulate baroreceptors in the pulmonary artery. The device controls the delivery of RCT and ART independently in either an open-loop or closed-loop fashion, the latter based upon a cardiac function assessment performed by the device.

1. Remodeling Control Therapy by Cardiac Resynchronization Pacing

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

It has also been found that CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

2. Anti-Remodeling Therapy by Modulating Autonomic Activity

As noted above, activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. In accordance with the present invention, electro-stimulatory means are employed to modulate autonomic activity, referred to as anti-remodeling therapy or ART. When delivered in conjunction with ventricular resynchronization pacing, such modulation of autonomic activity acts synergistically to reverse or prevent cardiac remodeling.

3. Exemplary Device Description

As shown in FIG. 1, an implantable cardiac device 100 for delivering CRT is typically placed subcutaneously or sub-muscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes the pacing pulses to be output in response to lapsed time intervals and sensed electrical activity (i.e., intrinsic heart beats not as a result of a pacing pulse). The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse with energy above a certain threshold is delivered to the chamber through a pacing channel which incorporates internal electrodes disposed near the chamber to be paced. Also shown in the figure is a satellite unit 110 which incorporates electrodes for neural stimulation and which communicates with the device 100 via a wireless link.

Figure 2:
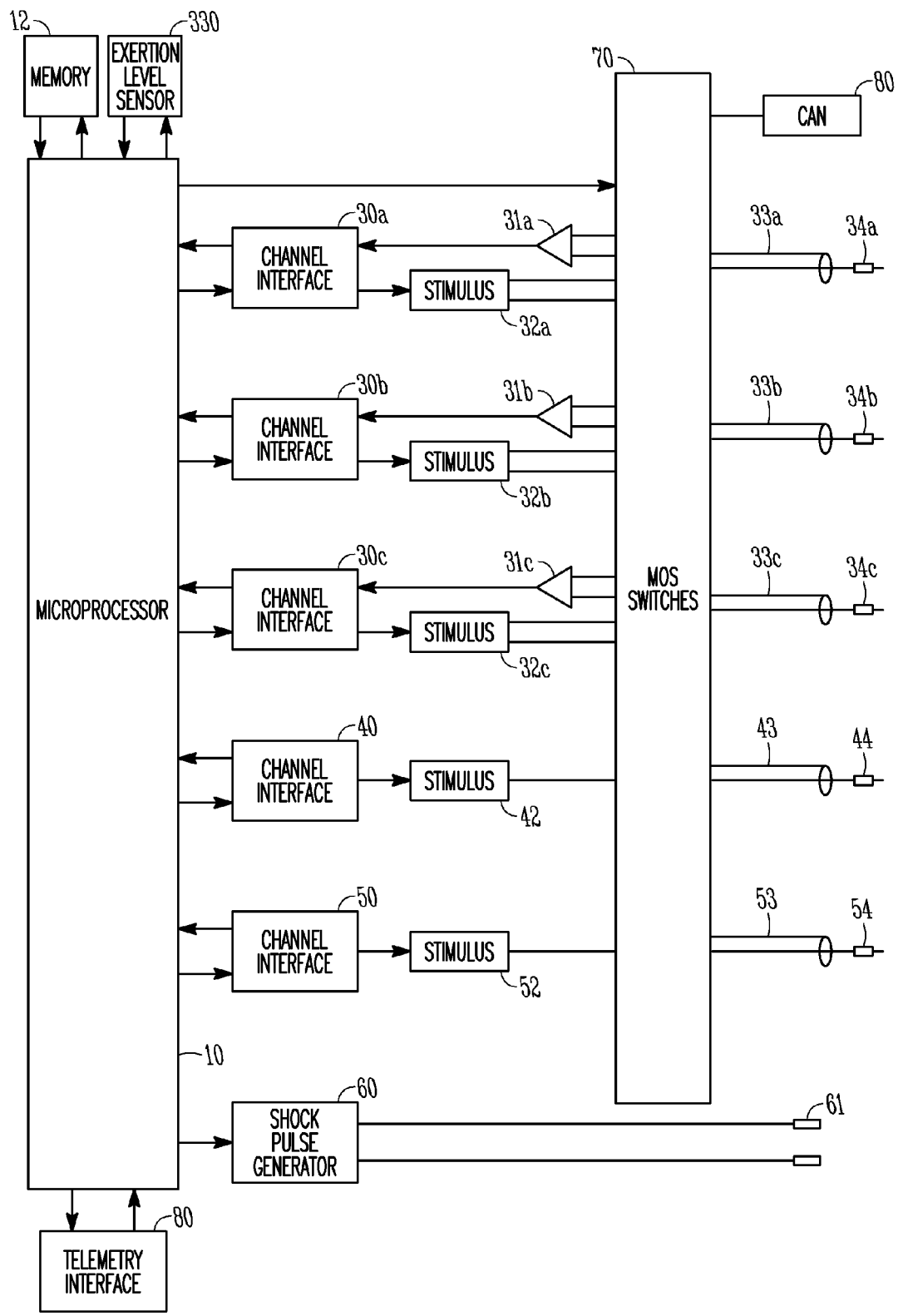
FIG. 2 is a system diagram of a cardiac device configured for multi-site stimulation and sensing.

FIG. 2 shows a system diagram of an exemplary microprocessor-based cardiac device. The device is equipped with multiple sensing and pacing channels which may be physically configured to sense and/or pace multiple sites in the atria or the ventricles. The device shown in FIG. 1 can be configured for cardiac resynchronization pacing of the atria or ventricles. The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 10 of the device is a microprocessor which communicates with a memory 12 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the FIG. 2 are three exemplary sensing and pacing channels designated "a" through "c" comprising bipolar leads with ring electrodes 34a-c and tip electrodes 33a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 80 serving as a ground electrode. A shock pulse generator 60 is also interfaced to the controller for delivering a defibrillation shock via a pair of shock electrodes 61 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 330 (e.g., an accelerometer, a minute ventilation sensor, or other sensor that measures a parameter related to metabolic demand) enables the controller to adapt the pacing rate in accordance with changes in the patient's physical activity and, as explained below, can enable the controller to modulate the delivery of neural stimulation and/or cardiac resynchronization pacing. A telemetry interface 40 is also provided which enables the controller to communicate with an external programmer or remote monitor.

Figure 3:
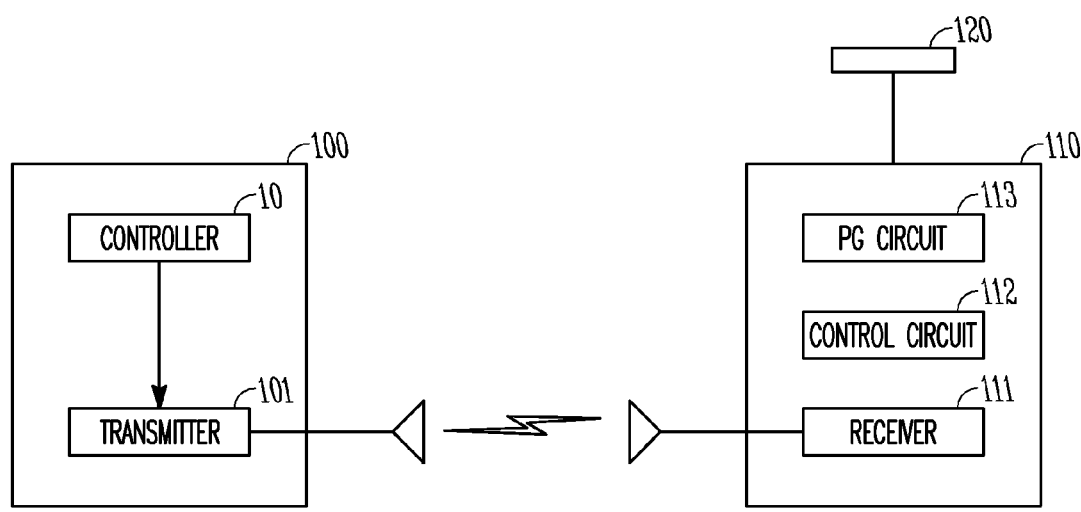
FIG. 3 illustrates an embodiment of an implantable device with RF-controlled satellite units for neural stimulation.

Neural stimulation channels are incorporated into the device for delivering parasympathetic stimulation and/or sympathetic inhibition, where one channel includes a bipolar lead with a ring electrode 44 and a tip electrode 43, a pulse generator 42, and a channel interface 40, and the other channel includes a bipolar lead with a ring electrode 54 and a tip electrode 53, a pulse generator 52, and a channel interface 50. Other embodiments may use unipolar leads in which case the neural stimulation pulses are referenced to the can or another electrode. The pulse generator for each channel outputs a train of neural stimulation pulses which may be varied by the controller as to amplitude, frequency, and duty-cycle. In this embodiment, each of the neural stimulation channels uses a lead which can be intravascularly disposed near an appropriate stimulation site, e.g., near a baroreceptor in the case of a sympathetic inhibition channel or near a parasympathetic nerve in the case of a parasympathetic stimulation channel. Other types of leads and/or electrodes may also be employed. A nerve cuff electrode may be used in place of an intravascularly disposed electrode to provide neural stimulation, where the electrode may be placed, for example, around the cervical vagus nerve bundle to provide parasympathetic stimulation or around the aortic or carotid sinus nerve to provide sympathetic inhibition. In another embodiment, the leads of the neural stimulation electrodes are replaced by wireless links, and the electrodes for providing parasympathetic stimulation and/or sympathetic inhibition are incorporated into satellite units. The wireless link may be, for example, a radio-frequency (RF) link or an acoustic link. FIG. 1 illustrates this wireless embodiment where the implantable device 100 communicates with such a satellite unit 110 via a wireless transmitter interfaced to the controller. The satellite unit 110 is an integrated assembly adapted for surgical implantation which includes a housing containing a battery and circuitry for outputting neural stimulation pulses to an external electrode which can clip around a target nerve (e.g., vagus, carotid sinus, or aortic nerve). FIG. 3 illustrates the functional components of the implantable device 100 and satellite unit 110 relevant to this embodiment. The implantable device includes a wireless transmitter 101 (e.g., either an RF transmitter or an acoustic transducer) interfaced to the controller 10 for transmitting commands, and the satellite unit 110 includes a wireless receiver 111 (e.g., either an RF receiver or a microphone for receiving acoustic signals) interfaced to control circuitry 112 for receiving the commands. The control circuitry 112 translates the received commands and causes pulse generation circuitry 113 to output appropriate stimulation pulses to the external electrode 120.

4. Assessment of Cardiac Function

In one embodiment of the invention, the delivery of RCT and/or ART is modulated in accordance with an assessment of cardiac function performed by the implantable device. One means by which cardiac function may be assessed is by measuring cardiac output and comparing it with the patient's measured exertion level. Cardiac output may be measured by an impedance technique in which transthoracic impedance is measured and used compute stroke volume. In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax.

Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output. The stroke volume integrated over time (or averaged and multiplied by heart rate) gives the patient's cardiac output. A look-up table or other function may be used to compute what cardiac output is considered adequate for a given exertion level. Measurement of cardiac output or a determination of the adequacy of the cardiac output may be used by the device to modulate the delivery of RCT and/or ART.

Another means for assessing cardiac function is by determining the autonomic balance of the patient. It is well-known that an increase in the activity of the sympathetic nervous system may be indicative of metabolic stress and the need for increased cardiac output. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac function is not adequate. A cardiac rhythm management device can be programmed to determine the LF/HF ratio by analyzing data received from its atrial ventricular sensing channels. The intervals between successive atrial or ventricular senses, referred to as beat-to-beat or BB intervals, can be measured and collected for a period of time or a specified number of beats. The resulting series of RR interval values is then stored as a discrete signal and analyzed to determine its energies in the high and low frequency bands as described above. Techniques for estimating the LF/HF ratio based upon interval data are described in commonly assigned U.S. patent application Ser. No. 10/436,876 filed May 12, 2003, now issued as U.S. Pat. No. 7,069,070, and Ser. No. 10/669,170 filed Sep. 23, 2003, the disclosures of which are hereby incorporated by reference.

Other means of assessing cardiac function may also be employed to modulate the delivery of ART and/or RCT. The impedance technique for measuring cardiac output discussed above may also be used to measure ventricular volumes at various stages of the cardiac cycle such as end-diastolic and end-systolic volumes and used to compute parameters reflective of cardiac function such as ejection fraction. The implantable device may also be equipped with other sensing modalities such as a pressure transducer. Such a pressure transducer may be attached to an intravascular lead and be appropriately disposed for measuring diastolic filling pressures and/or systolic pulse pressures.

5. Exemplary Implementations

In an exemplary embodiment of the invention, an implantable device for delivering cardiac therapy to post-MI patients includes one or more pacing channels for delivering pacing pulses to one or more ventricular sites and a sympathetic inhibition channel for stimulating nerves which inhibit sympathetic nerve activity. The controller is programmed to deliver remodeling control therapy (RCT) by delivering ventricular pacing in a cardiac resynchronization mode which pre-excites a region of the ventricular myocardium so as to mechanically unload that region during systole. The cardiac resynchronization therapy may be delivered as biventricular pacing where one of the ventricles is pre-excited relative to the other as determined by a programmed biventricular offset interval. Alternatively, in patients suffering from delayed activation of the left ventricle, a left ventricle-only resynchronization pacing mode may be employed. In another embodiment, the pacing therapy may be delivered as multi-site ventricular pacing where at least one of the ventricles is paced at a plurality of sites so as to pre-excite one or more of the sites relative to the other sites. In any case, the ventricular pacing may be delivered in a non-atrial tracking mode where a ventricular escape interval is defined between ventricular paces, or in an atrial tracking mode where the ventricular paces are delivered after a defined atrio-ventricular escape interval following an atrial sense. In a patient who is chronotropically incompetent, an atrial pacing channel may also be provided for pacing the atria, with the ventricular pace(s) delivered upon expiration of the atrio-ventricular escape interval following the atrial pace.

The controller is further programmed to delivery anti-remodeling therapy (ART) in conjunction with the RCT by inhibiting sympathetic nerve activity via the sympathetic inhibition channel. The sympathetic inhibition channel may include a pulse generator for outputting neural stimulation pulses and a lead incorporating an electrode adapted for disposition near an arterial baroreceptor or afferent nerve of a baroreflex arc. Stimulation of the baroreflex arc then results in inhibition of sympathetic activity. The electrode of the sympathetic inhibition channel may be intravascularly positioned in a blood vessel or elsewhere proximate to a baroreceptor or afferent nerve such as in a pulmonary artery or a cardiac fat pad. In another embodiment, the device may further include a parasympathetic stimulation channel, where the anti-remodeling therapy delivered by the controller further includes stimulation of parasympathetic nerve activity, and the parasympathetic stimulation channel includes a pulse generator for outputting neural stimulation pulses and an electrode for stimulating a parasympathetic nerve. The electrode may be a nerve cuff electrode adapted for disposition around a parasympathetic nerve or an intravascular electrode for transvascularly stimulating a parasympathetic nerve adjacent to a blood vessel. As described above, for either the sympathetic inhibition channel or the parasympathetic stimulation channel, the electrode and pulse generator may also be incorporated into a satellite unit which includes an RF receiver. The implantable device then further comprises an RF transmitter interfaced to the controller for controlling the operation of the satellite unit via an RF link.

Figure 4A:
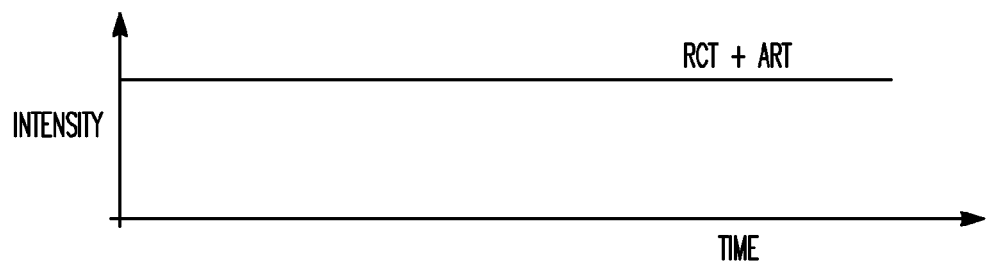
FIGS. 4A-D illustrate examples of how the intensities of ART and RCT may be individually time-varied.
Figure 4B:
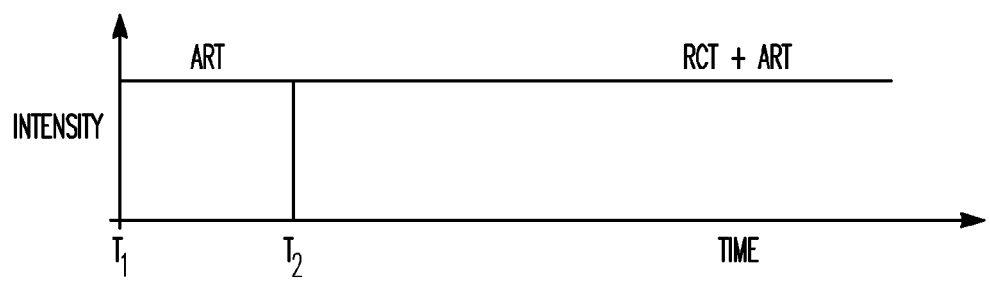
Figure 4C:
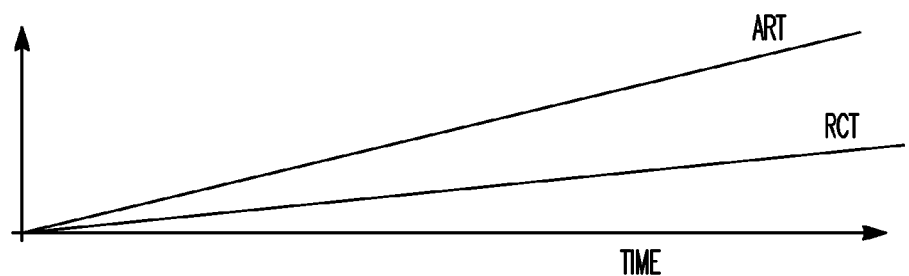
Figure 4D:
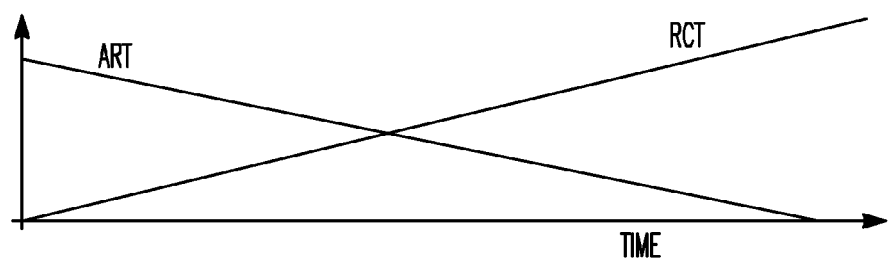

The device may be programmed to deliver RCT and ART in open-loop fashion where the RCT and ART are delivered simultaneously or separately at programmed intervals. The RCT and ART may be delivered at a constant or time-varying intensity, where the intensity of the ART may be adjusted by varying the amplitude, frequency, or duty-cycle of the neural stimulation pulses, and the intensity of the RCT may be adjusted by varying one or more parameters which affect the amount of pre-excitation delivered to the ventricles such as the biventricular offset interval and the atrio-ventricular escape interval. FIGS. 4A through 4D illustrate examples of how the level of RCT and ART may be varied with respect to time. In FIG. 4A, both RCT and ART are delivered simultaneously with each type of therapy maintained at a constant intensity. In FIG. 4B, both RCT and ART are delivered at a constant intensity, but ART starts at a time $T_1$ while RCT starts at a time $T_2$. In FIGS. 4C and 4D, the intensity of each type of therapy is modulated with respect to time. FIG. 4C shows the intensity of both the RCT and ART increasing with respect to time, while FIG. 4D shows the intensity of the RCT increasing while the intensity of the ART decreases. The relative intensities of sympathetic inhibition and parasympathetic stimulation may also be separately modulated.

In another embodiment, the device is programmed to deliver RCT and ART in closed-loop fashion, where the intensities of RCT and ART are modulated in accordance with an assessment of cardiac function performed by the controller. The device may also separately modulate the intensities of parasympathetic stimulation and sympathetic inhibition which are delivered as part of the ART in accordance with the assessment of cardiac function. Cardiac function may be assessed by the device using several different modalities, either alone or in combination. In one embodiment, the device incorporates a sensor for measuring cardiac output, and the controller is programmed to modulate the delivery of RCT and ART in accordance with the measured cardiac output. As described above, such a cardiac output sensor may be a transthoracic impedance measuring circuit. Another means for assessing cardiac function is an arterial blood pressure sensor, where the controller is programmed to modulate the delivery of RCT and ART in accordance with the measured blood pressure. The blood pressure sensor may take the form of a pressure transducer and lead adapted for disposition within an artery. Alternatively, a measure of the patient's respiratory activity taken by a minute ventilation sensor may be used as a surrogate for blood pressure. Cardiac function may also be assessed by measuring the patient's exertion level (e.g., using either a minute ventilation sensor or an accelerometer) together with a measure of cardiac output and/or blood pressure, where the controller is then programmed to modulate the delivery of RCT and ART in accordance with the combined measurements.

In another embodiment, the cardiac function assessment includes an assessment of the patient's autonomic balance. Autonomic balance may be assessed directly with a sensing channel for measuring electrical activity in sympathetic and parasympathetic nerves with appropriately positioned sensing electrodes, or if the patient is chronotropically competent, by measuring the intrinsic heart rate. As described above, measuring heart rate variability provides one means for assessing autonomic balance. Thus, the device may include circuitry for measuring and collecting time intervals between successive intrinsic beats, referred to as a BB interval, where the BB interval may be an interval between successive atrial or ventricular senses. The device stores the collected intervals as a discrete BB interval signal, filters the BB interval signal into defined high and low frequency bands, and determines the signal power of the BB interval signal in each of the low and high frequency bands, referred to as LF and HF, respectively. The device then computes an LF/HF ratio and assesses autonomic balance by comparing the LF/HF ratio to a specified threshold value.

In certain embodiments, data gathered by the device in performing the assessment of cardiac function performed is transmitted to a remote monitor via an RF telemetry link. The remote monitor may record the data for later analysis by a clinician and/or transmit it to another location over a network such as the internet. In response to network communications, the remote monitor may also program the implantable device via the RF telemetry link in order to modify the delivery of RCT and ART.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering cardiac therapy to a patient, comprising:
   one or more pulse generators for incorporating into one or more pacing channels for delivering pacing pulses and for incorporating into a parasympathetic stimulation channel for delivering neural stimulation pulse in order to stimulate parasympathetic nerve activity;
   a sensor for measuring blood pressure;
   a controller for controlling the delivery of pacing pulses to one or more ventricular sites during a cardiac cycle in accordance with a programmed pacing mode;
   wherein the controller is programmed to deliver remodeling control therapy (RCT) by controllably delivering ventricular pacing in a manner which pre-excites a region of the ventricular myocardium so as to mechanically unload that region during systole;
   wherein the controller is further programmed to deliver anti-remodeling therapy (ART) by controlling stimulation of parasympathetic nerve activity via the parasympathetic stimulation channel;
   wherein the controller is programmed to perform an assessment of cardiac function and to modulate the delivery of the RCT and ART in accordance with the assessment of cardiac function, wherein the assessment of cardiac function includes a measurement of blood pressure; and,
   wherein the ART is modulated in response to the assessment of cardiac function by varying the amplitude of the neural stimulation pulses.

2. The device of claim 1 further comprising a neural inhibition channel for inhibiting sympathetic nerve activity and wherein the anti-remodeling therapy delivered by the controller further includes inhibition of sympathetic nerve activity.

3. The device of claim 1 further comprising a nerve cuff electrode for incorporating into the parasympathetic stimulation channel and adapted for disposition around a parasympathetic nerve.

4. The device of claim 1 further comprising an electrode adapted for intravascular disposition for incorporating into the parasympathetic stimulation channel in order to transvascularly stimulate a parasympathetic nerve adjacent a blood vessel.

5. The device of claim 1 further comprising a cardiac output sensor for producing a measurement of cardiac output and wherein the cardiac function assessment further includes the cardiac output measurement.

6. The device of claim 5 wherein the cardiac output sensor is a trans-thoracic impedance measuring circuit.

7. The device of claim 1 further comprising an exertion level sensor for producing a measurement of the patient's exertion level, and wherein the cardiac function assessment further includes the exertion level measurement.

8. The device of claim 7 wherein the exertion level sensor is a minute ventilation sensor.

9. The device of claim 1 further comprising a sensing amplifier for incorporating into a sensing channel for detecting cardiac activity; circuitry for producing a measurement of heart rate variability and for assessing the patient's autonomic balance based on the heart rate variability measurement; and wherein the cardiac function assessment further includes the assessment of the patient's autonomic balance based upon heart rate variability measurement.

10. The device of claim 1 wherein the RCT is modulated in response to the assessment of cardiac function by varying the extent of pre-excitation provided to a ventricular pacing site.

11. The device of claim 1 wherein the ART is further modulated in response to the assessment of cardiac function by varying the frequency or duty cycle of parasympathetic stimulation pulses.

12. The device of claim 1 wherein the controller is programmed to deliver the RCT as biventricular pacing so as to pre-excite one of the ventricles relative to the other.

13. The device of claim 1 wherein the controller is programmed to deliver the RCT as multi-site ventricular pacing where at least one of the ventricles is paced at a plurality of sites so as to pre-excite one or more of the sites relative to the other sites.

14. The device of claim 1 wherein the controller is programmed to deliver the RCT as left ventricle-only pacing which pre-excites the left ventricle relative to the right ventricle during systole.

15. A method for operating a cardiac device to deliver cardiac therapy to a patient, comprising:
  delivering remodeling control therapy (RCT) by controllably delivering ventricular pacing through one or more pacing channels in accordance with a programmed mode in a manner which pre-excites a region of the ventricular myocardium so as to mechanically unload that region during systole;
  delivering anti-remodeling therapy (ART) by controlling stimulation of parasympathetic nerve activity via a parasympathetic stimulation channel;
  measuring blood pressure; and,
  performing an assessment of cardiac function and modulating the delivery of the RCT and ART in accordance with the assessment of cardiac function, wherein the assessment of cardiac function includes the measured blood pressure and wherein the ART is modulated by varying an amplitude of the parasympathetic nerve stimulation.

16. The method of claim 15 further comprising measuring exertion level wherein the assessment of cardiac function further includes the measured exertion level.

17. The method of claim 15 further comprising measuring heart rate variability, assessing the patient's autonomic balance based upon the measured heart rate variability, and wherein the assessment of cardiac function further includes the assessment of the patient's autonomic balance based upon heart rate variability.

18. The method of claim 15 wherein the anti-remodeling therapy further includes inhibition of sympathetic nerve activity.

19. The method of claim 15 further comprising modulating the RCT in response to the assessment of cardiac function by varying the extent of pre-excitation provided to a ventricular pacing site.

20. The method of claim 15 further comprising modulating the ART in response to the assessment of cardiac function by varying the frequency or duty cycle of parasympathetic stimulation pulses.

* * * * *